(12) United States Patent
Moreau

(10) Patent No.: US 6,596,861 B1
(45) Date of Patent: Jul. 22, 2003

(54) METHOD FOR THE REDUCTIVE AMINATION OF POLYSACCHARIDES

(75) Inventor: Monique Moreau, Lyons (FR)

(73) Assignee: Aventis Pasteur S.A., Lyons Cedex (FR)

( * ) Notice: Subject to any disclaimer, the term of this patent is extended or adjusted under 35 U.S.C. 154(b) by 0 days.

(21) Appl. No.: 09/936,072

(22) PCT Filed: Mar. 10, 2000

(86) PCT No.: PCT/EP00/02748

§ 371 (c)(1),
(2), (4) Date: Jan. 18, 2002

(87) PCT Pub. No.: WO00/55210

PCT Pub. Date: Sep. 21, 2000

(30) Foreign Application Priority Data

Mar. 12, 1999 (EP) ............................................ 99420071

(51) Int. Cl.$^7$ ................................................. C07H 1/00
(52) U.S. Cl. ............................. 536/123.1; 536/123.12; 536/124
(58) Field of Search .............................. 536/123.1, 51, 536/124, 123.12

(56) References Cited

U.S. PATENT DOCUMENTS 5,681,570 A * 10/1997 Yang ..................... 424/197.11

FOREIGN PATENT DOCUMENTS

JP 05339300 3/1994

OTHER PUBLICATIONS

Rajendar S. Varma and Rajendar Dahiya Tetrahedron, 1998, vol. 54, pp 6293–6298.*

Paoletti, Lawrence C. et al The Journal of Biological Chemistry, 1990, vol. 265, No. 30, pp 18278–18283.*

Varma, R.S. and R. Dahiya. "Sodium Borohydride on Wet Clay: Solvent–Free Reductive Amination . . . Using Microwaves." *Tetrahedron*. vol. 54, pp. 6293–6298 (1998).

Rechsteiner, Tetrahedron Letters 34, 5071–5074 (1993).

Loupy, Fondemaental, OCL No. 1, vo. 1: 62–68 (1994) (English translation).

* cited by examiner

*Primary Examiner*—James O. Wilson
*Assistant Examiner*—G. Krishnan
(74) *Attorney, Agent, or Firm*—McDonnell Boehnen Hulbert & Berghoff

(57) ABSTRACT

The invention relates to a method for reductive amination of polysaccharides which comprises subjecting a reaction mixture comprising a polysaccharide, an amino compound and a reducing agent, to microwave radiation for a period of time sufficient to aminate the polysaccharide.

18 Claims, No Drawings

METHOD FOR THE REDUCTIVE AMINATION OF POLYSACCHARIDES

The present invention relates to (i) a method for the reductive amination of polysaccharides, particularly useful in a process for conjugating polysaccharides to polypeptides, and (ii) produced—by—process polysaccharide-polypeptide conjugates and use thereof in pharmaceutical compositions e.g., vaccines.

In recent years, there has been considerable interest in conjugates of polysaccharide and polypeptide molecules and methods of preparation of such conjugates. In the area of vaccine development, for example, purified bacterial capsular polysaccharides have been covalently attached to protein molecules to produce protein-polysaccharide conjugate vaccines. Purified capsular polysaccharide from *Haemophilus influenzae* type b has been covalently attached to a number of protein molecules, e.g. diphtheria toxoid and tetanus toxoid protein, and these conjugates are known to elicit a Tell dependent immune response in the infant population. This feature has allowed the development and licensure of effective vaccines against disease caused by the bacterium *Haemophilus influenzae* type. This approach of preparing conjugate vaccines has also been extended to other capsular polysaccharides, such as those purified from *Neisseriae meningitidis* and *Streptococcus pneumoniae*.

Polysaccharides usually are T-independent antigens unable to elicit an anamnestic (memory) response. Additionally, they are not at all or poorly immunogenic in infants. It is well-known that such disadvantages may be overcome by conjugating the polysaccharides to a carrier polypeptide.

Polysaccharides may be coupled to polypeptides directly or via spacer/linker molecules, according to a variety of methods. Some of them take advantage of the reducing end present in all polysaccharides. Indeed, this extremity may be easily reacted with functional groups such as amino groups. In particular, it may be subjected to reductive amination under mild conditions that is, at low temperature (usually at about 50° C.), in the presence of an appropriate reducing agent. Reductive amination is a classical reaction of carbonyl and amino groups, and is the result of 2 successive reactions:

Formation of imine: 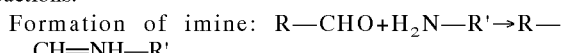

Reduction of the double bond in the presence of a reducing agent: 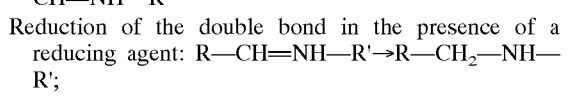

wherein R is the polysaccharide and R' an amino donor. Imine formation usually evolves toward an equilibrium state, the final product being therefore partially aminated (some molecules remaining non-aminated).

The simplest method involves reacting the terminal reducing sugars of polysaccharides with amino groups of a polypeptide (e.g., side chain amino groups of lysine residues), in the presence of a reducing agent. As a result, the polysaccharide is coupled to the polypeptide via a direct covalent bound.

More sophisticated procedures involve reacting the terminal reducing sugars of the polysaccharide with a linker or a spacer molecule bearing at least one amino group, in the presence of a reducing agent, so as to produce an activated polysaccharide which may be further conjugated to a polypeptide according to a variety of conventional conjugation methods.

The polysaccharide terminal reducing sugar is not the only polysaccharide functional groups that can be subjected to reductive amination. Functional groups available for linkage to amino groups also include e.g. carbonyls, such as aldehydes and ketones, present all along the carbohydrate chain. Alternatively, they may even be created on purpose by a chemical treatment.

As described above, reductive amination is a chemical reaction widely used in polysaccharide conjugation methods. However, this reaction is time-consuming, taking on the order of days to perform. It is believed that the imine formation is a very slow reaction that constitutes a limiting step of the global reductive amination reaction.

Also, the ultimate yield of aminated polysaccharide may be compromised by the formation, over time, of undesirable secondary reaction products. Undesirable secondary reaction events include e.g. the reversal to the non-reduced form of the polysaccharide and more importantly, the formation of degradation products. Reducing agents that can be used for reducing the imine bond are also capable of reducing the terminal aldehyde function of the polysaccharide. Indeed, hydrides other than cyanoborohydride can equally reduce the aldehyde and the imine bond. Cyanoborohydride preferentially reduces the imine bond.

That chemical reactions in general can be accelerated by heating is well-known. Indeed, reductive amination of polysaccharides is conventionally carried out at a temperature about 15–50° C., the reaction mixture being placed in a water bath. More elevated temperatures (e.g., above 100° C.) are not appropriate, because polysaccharides could be degraded or denatured.

In a more general manner, the use of microwave ovens, per se, to accelerate certain reactions, such as organic synthesis, has also been described. To our knowledge, Loupy, et al. Tetrahedron Letters (1996) 37:8177 is the only document that discloses the use of rmicrowave radiation in a reductive amination procedure. However, the reaction employed by Loupy et al is a very special reductive amination (namely, the Leuckart reaction), which is only suitable for low molecular weight carbonyl compounds, not for polysaccharides. In particular, the Leuckart reaction is characterized by harsh reaction conditions e.g., high temperatures (maximal reaction temperatures are far above 100° C.). The Leuckart reaction also differs from reductive amination under mild conditions in that reductive amination is accompanied by decarboxylation (see the reaction scheme on page 8180 of Loupy et al). No such decarboxylation occurs when reductive amination is carried out under mild conditions.

Surprisingly, it has now been found that the time necessary for reductive amination of polysaccharides can be dramatically reduced while submitting the reaction mixture to microwave radiation. It is believed that microwave radiation may accelerate both the imine formation and the reductive amination step. In particular, reductive amination using a mild reducing agent such as cyanoborohydride is a slow reaction when performed according to conventional practice and it may dramatically accelerated under microwave radiation.

Also surprising was the finding that this procedure allows for rapid reductive amination of polysaccharides of interest under relatively mild conditions, such that essential antigenic determinants within the polysaccharides are retained. This is indeed extremely important in that conjugate vaccines must be prepared in such a way as to retain, as much as possible, the structure and conformation of the component materials, for example the polysaccharides and proteins. Critical antigenic determinants are often comprised of portions of the structure and/or conformation of such molecules, and if such determinants are not retained then the resulting conjugate vaccine will be incapable of inducing the desired immune response. For example, O-acetyl or phosphate groups on polysaccharide are important antigenic determinants and can be quite labile. Surprisingly, these important determinants are not affected by the microwave-enhanced reductive amination procedure of the present invention.

Even more surprising was the finding that, in contrast to the classical reductive amination procedure, the formation of undesirable secondary reaction products is limited, compared to what is obtained in a conventional reductive amination procedure. The implications of this latter finding are quite significant Indeed, additional reaction cycles can be performed to increase the degree of amination of the polysaccharide. This, in turn, provides the means to prepare conjugates wherein more polysaccharides are added to identical amount of polypeptides and therefore to improve conjugation yield.

In brief, the present invention provides a means for dramatically reducing the overall reaction time for reductive amination, while at the same time providing the means to significantly increase the yield of the product of interest (aminated polysaccharide), for example by performing multiple rounds of reductive amination in the microwave.

Therefore, the present invention provides a method for reductive amination of polysaccharides which comprises:
 (i) subjecting a reaction mixture comprising a polysaccharide, an amino compound and a reducing agent, to microwave radiation for a period of time sufficient to aminate the polysaccharide;
 (ii) (a) subjecting a reaction mixture comprising a polysaccharide and an amino compound to microwave radiation polysaccharide for a period of time sufficient to allow the formation of an imine compound, (b) adding a reducing agent to the reaction mixture obtained in (a) so that the polysaccharide be aminated;
 (iii) (a) adding an amino compound to a polysaccharide so that an imine compound is formed, (b) adding a reducing agent to the reaction mixture obtained in (a) and, (c) subjecting the reaction mixture obtained in (b) to microwave radiation for a period of time sufficient to aminate the polysaccharide; or
 (iv) (a) subjecting a reaction mixture comprising a polysaccharide and an amino compound to microwave radiation for a period of time sufficient to allow the formation of an imine compound, (b) adding a reducing agent to the reaction mixture obtained in (a) and, (c) subjecting the reaction mixture obtained in (b) to microwave radiation for a period of time sufficient to aminate the polysaccharide.

Apart from the use of microwave radiation, reductive amination can be performed in a conventional manner. For example, polysaccharides can be aminated under mild conditions, according to Borch et al, J. Amer. Chem. Soc. (1971) 93:2897 or Gray et al, Arch. Biochem. Biophys (1974) 163:426. It is within the skills of the man in the art to determine the suitable amounts of the products to be reacted. In a general manner, it is however indicated that the amino compound is advantageously added in a large molar excess in relation to the polysaccharide, especially when the amino donor is a homobifunctional molecule.

As already mentioned above, the extent of reductive amination among a population of polysaccharide molecules is usually incomplete; some molecules remaining non-aminated. Some of them may also be partially aminated (not all of the functional groups being reduced). Altogether, the term "aminated polysaccharide" is accordingly understood to encompass a partially aminated polysaccharide molecule as well as an heterogeneous population of aminated and non-aminated molecules.

The reaction mixture is advantageously in an aqueous medium. It may also be in an organic solvent e.g., depending upon the choice of the reducing agent. For example when the reducing agent is pyridine borane, it is appropriate to use an organic solvant. In a most preferred embodiment, the polysaccharide the amino compound and the reducing agent are in a buffer solution in order to avoid pH variability. In a general manner, reductive amination can be performed over a pH range of 5 to 10, advantageously of 6 to 8 preferably at about pH 7.

It is also recommended to use a buffer solution, especially when the polysaccharide is a neutral polysaccharide. Indeed, in order to benefit from microwave radiation, it is necessary for the polysaccharides to have an overall dipole moment, which allows the molecule to move in the alternative field of microwaves and consequently, to be more reactive. Charged polysaccharides naturally comply more or less to this criteria In order to perform reductive amination on neutral polysaccharides, it is preferable that they be treated in some way so as to introduce a net charge or dipole. The use of a buffer solution can serve this purpose. Electrolyte buffers such as borate, mobyldate, tungstate, stannate, and arsenite buffers are more particularly suitable. This approach can be demonstrated for dextran. The dextran solution can be prepared in phosphate or borate buffer. Borate binds to the hydroxyl groups of the sugar residues within dextran, resulting in a stable, negatively charged complex. A solution of dextran in borate, subjected to the same reductive amination conditions as described in Example 1 above, undergoes rapid reductive amination in the microwave apparatus relative to that achieved in the water bath (or that achieved in phosphate buffer under either incubation condition). The extent of amination achieved by incubating the dextran-borate solution in the microwave for 1 hour is comparable to that obtained after 48 hours of incubation in the water bath. (Table 2).

For charged polysaccharides, buffers other than borate and equivalents are usually preferred. For example, a phosphate buffer is suitable.

In order to optimize reductive amination, the selection of the most suitable buffer for a given polysaccharide can readily accomplished empirically. If a polysaccharide does not yield an acceptable level of aminated product in phosphate buffer, then the reaction should be repeated in borate buffer.

For purposes of the present invention, conventional microwave ovens may be used but they are not preferred. Indeed, in such ovens, the temperature usually raises 100° C. (especially when working with small amount) and it is difficult to keep control of the temperature so that it is maintained below 100° C. Those skilled in the art of carbohydrate chemistry will readily appreciate the limitation inherent in working with polysaccharides at elevated temperatures with labile antigenic epitopes. Additionally, over 100° C., such materials form viscous syrups which can be difficult if not impossible to work with. Another limitation of the conventional microwave is the fact that the individual beams of microwave radiation are scattered in a random fashion throughout the interior of the apparatus. Thus, it can be difficult in practice, to control the extent of radiation of experimental samples, particularly if such samples comprise a relatively small volume (e.g., 10 ml or less).

Certain of these obstacles have been overcome by development of microwave apparatuses capable of providing a focused or localized beam of microwave radiation at a specified position within the apparatus. The reaction mixture can conveniently be placed in such position, ensuring that such reaction mixture will be exposed to the microwave radiation. One such microwave apparatus is the SYNTHE-WAVE™ 402 instrument manufactured and sold by Prolabo, Fontenay-Sous-Bois, France, the use of which is preferred for the purposes of the present invention. This instrument uses reflecting means to focus the microwave radiation across a path into which a reaction tube is placed. The SYNTHEWAVE™ 402 instrument also measures the temperature of the reaction caused by the microwave radiation by means of infrared detection and modulates the extent of microwave treatment in order to keep the temperature constant. In this way, it is possible to subject samples to a range of temperatures below 100° C.

Of course, those skilled in the art will recognize that other types of microwave apparatus may be designed or modified in such a way as to be used in the present invention, without departing from the spirit of the invention. For example, if the reaction volume is sufficiently large, e.g., 100 ml or more, it is possible to perform the reaction in a conventional microwave, controlling the extent of microwave treatment manually or in conjunction with a temperature-detecting and—regulating means as described for the apparatus designed by Prolabo.

In the electromagnetic spectrum, microwaves are positioned in the wavelength values comprised between one centimeter and one meter.

As explained above, the reaction temperature is an important parameter that shall be kept under control. Advantageously, the reaction is achieved at a temperature not exceeding 100° C., preferably 60° C., more preferably 50° C.

The other experimental parameters that allow for fine adjustments of the degree of amination achieved, include i.a., the choice of buffer used in the reaction mixture as explained above, and the length of time of the reaction. Defining conditions to obtain the desired extent of amination is a relatively straightforward process involving selection of buffer composition and defining the incubation times.

The kinetic of the reductive amination reaction typically adopts a curve with a plateau and the reaction time is defined as the period of time necessary for reaching the plateau. While all polysaccharides studied undergo more rapid reductive amination in the microwave than in the conventional 50° C. water bath, certain polysaccharides can be reductively aminated more easily than others. For example, Vi polysaccharide from *Salmonella typhi* can be reductively aminated in as little as 15 min, whereas incubation for 1 hour is preferred when working with Dextran. Accordingly, it is indicated that a reaction time of from 1S min to 4 hours is generally suitable and as already explained above, this represents a significant improvement over the prior art technique.

As explained above, reductive amination is a two-step reaction. As reflected in the statement of the invention, it is possible to perform both steps separately i.e., to allow first the reaction of the polysaccharide and the amino compound so as to form an imine bound and then, to add a reducing agent in order to reduce the imine bound. When strong reducing agents such as borohydride are used, the second step is achieved rather quickly under conventional conditions, and therefore there is little advantage to perform it under microwave radiation, at least as far as the reaction time is of concern. When a mild reducing agent such as cyanoborohydride is used, it is preferred to achieve the second step under microwave radiation in order to accelerate the reaction and also to selectively obtain the desired reduced form.

When a plateau is reached, this does not mean that all the carbonyl groups present on the polysaccharide molecules have been reductively aminated; number of these carbonyl groups remain non-reduced, especially when cyanoborohydride is used as a reducing agent. Under these circumstances, it is appropriate to consider that the product obtained by the method of the invention contains aminated and non-aminated polysaccharide molecules. Moreover, when the polysaccharide molecule species contains more than one carbonyl group, a molecule may only be partially aminated. Globally the product obtained by the method of the invention may be described as being partially aminated, as already mentioned herein above. The fact that a plateau is reached without the reagents being totally consummated, is probably due to the formation of inhibitory by-products.

The reaction efficiency may be evaluated while measuring the extent of amination that is the amino group:polysaccharide rate (weight:weight). The number of reducing end groups can additionally be determined using the method of Park & Johnson, J. Biol. Chem. (1949) 181:149.

When desirable, the extent of amination may be substantially increased by performing successive rounds of reductive amination if there remains sufficient carbonyl groups available for further reductive amination after the plateau is reached in the first round. In effect, the product of the first reductive amination round can be recovered and purified from the reaction medium including the reagents ; then the amino compound and reducing agent can freshly be added and the reaction performed as before. The reaction may be repeated one or more additional times. Such a way of proceeding is made possible even at the industrial scale, since the reaction time is dramatically reduced by the use of microwave radiation. This opens new avenues for preparing polypeptide-polysaccharide conjugates by providing, on a polysaccharide bearing reducing groups resulting from a chemical reaction such as periodic oxydation, more sites capable of reacting with a carrier polypeptide. It is especially appropriate to perform successive rounds of reductive amination when a reducing agent such as cyanoborohydride is initially used.

The choice of the reducing agent can be conventionally made by those skilled in the art Reducing agents useful in the method of the invention include hydrogen in the presence of a catalyst; a hydride such as borohydride ($BH_4$), Al Li $H_4$, pyridine borane ($PyBH_3$) or cyanoborohydride such as $NaCNBH_3$. Borohydride and cyanoborohydride which allow for reaction in an aqueous medium, are particularly preferred.

The method of the present invention can be applied to any type of polysaccharide, in particular fungal or bacterial polysaccharides. Bacterial polysaccharides can be capsular polysaccharides or the O-antigen moiety (also called O-specific side chain) of cell-wall lipopolysaccharides (LPS), which comprises 2-deoxy-keto-octulosonic acid (KDO). As a matter of example, a bacterial polysaccharide for use in the present invention can be a polysaccharide (e.g. a capsular polysaccharide) of *Streptococcus pneumoniae* (in particular those of serotypes 1, 3, 4, 5, 6B, 7F, 9V, 14, 18C, 19F and 23F), *Haemophilus influenzae, Neisseria meningitidis* (in particular those of groups A, B, C, W135 and Y), *Escherichia coli, Salmonella typhi, Salmonella typhimurium, Chlamydia neoformans, Klebsiella pneumoniae, Staphylococcus aureus*, and *Pseudomonas aeruginosa*. The bacterial polysaccharide can also be the O-antigen moiety of LPS of *Moraxella catarrhalis*, non-typeable Haemophilus, *Bordetella pertussis, Helicobacter pylori, Salmonella typhi, Salmonella paratyphi*, Shigella or *Chlamydia pneumoniae*. Cell wall fungal polysaccharides may be, for example, from Candida, *Cryptococcus neoformans* or Hansenula.

Those skilled in the art will readily appreciate that the utility of the method according to the invention does not depend on the chemical structure of the polysaccharide:a very large number of structurally and chemically disimilar polysaccharides may be aminated. This includes neutral polysaccharides (e.g., Dextran), positively charged polysaccharides (e.g., polysaccharide Vi and polygalacturonic acid), neutral polysaccharides with N-acetyl groups (e.g., pneumo type 14), neutral polysaccharides with phosphate groups (e.g., pneumo type 18C), and neutral polysaccharides with O-acetyl groups and derivatized side chains (e.g. pneumo type 7F).

As already explained above, polysaccharides exhibit a reducing end. In addition to this, some polysaccharides may also exhibit all along the carbohydrate chain, functional groups such as carbonyls, that are available for reductive amination. Ketone groups present in the KDO extremity of the O-antigen moiety of LPS are available as well. If desired, reducing groups may also be introduced on the polysaccharide chain prior to reductive amination. For example, it is well-known that reducing groups may be created by periodate oxidation, all along a polysaccharide chain (except that when the *Haemophilus influenzae* polysaccharide is used, reducing groups are created upon cleavage of the polysaccharide chain).

Polysaccharides of interest to the present invention may be obtained from any of a number of potential sources. Several such polysaccharides, e.g., pneumococcal polysaccharide types 6A, 14, 19F and 23F are available from the American Type Culture Collection. They may also be extracted and purified directly from microorganisms. Polysaccharides may be prepared from capsular polysaccharide of bacteria or from lipopolysaccharides, using conventional techniques. See, e.g., Porro, U.S. Pat. No. 5,153,312 and EP 0 477 508 for a discussion of preparation procedures.

While the invention has thus far been described mainly in terms of bacterial polysaccharides, it is equally applicable to polysaccharides from other sources. Examples provided in support of the present invention include, e.g., dextran and polygalacturonic acid, both of which are obtained from plants.

In a general manner, by "polysaccharide" is meant a carbohydrate chain, regardless of the length of the chain, ie., regardless of the amount of repeat units. Accordingly, this term also includes oligosaccharides. The carbohydrate chain can also be attached to other component such as KDO.

As may be easily understood, the molecular weight of a polysaccharide chain depends upon (i) the molecular weight of the repeat unit and (ii) the amount of repeat units composing the chain. Also, the term "polysaccharide" designs a population of polysaccharide chains of various lengths and therefore a given polysaccharide size usually corresponds to a mean value.

It is indicated that a convenient polysaccharide size can range from e.g., four repeat units to 2,000 repeat units. The size is advantageously from eight, preferably twelve, more preferably twenty, most preferably thirty repeat units to advantageously 1,000 preferably 800, most preferably 500 repeat units.

In a general manner, the size of the polysaccharide chain is not a critical parameter for performing reductive amination. Depending on the further use of the aminated polysaccharide, it may however be more appropriate to use polysaccharide having a moderate size. In particular, capsular polysaccharides extracted from bacteria may exhibit a huge size and in some cases, it may be desirable to reduce the mean size value by depolymerization prior to reductive amination. Depolymerization or fragmentation (both terms are used interchangeably) may conventionally be effected by chemical or mechanical means e.g., WO 93/7178 describes a fragmentation method by reductive oxidation (ORD). Some such procedures are also detailed by Porro, U.S. Pat. No. 5,153,312.

For purposes of the present invention, native polysaccharide, oligosaccharide, partially depolymerized or fragmented polysaccharide or saccharide are used interchangeably. Reductive amination can be performed on any such polysaccharide, subject only to retention of antigenic determinants.

For use in the present invention, the amino compound may be any molecule or reagent capable of providing amino groups under the conditions described herein.

In one embodiment, it can be a polypeptide. In this case, the product directly obtained by reductive amination is a polysaccharide-polypeptide conjugate wherein the reducing end (s) of the polypeptide is (are) linked to the side-chain amino groups of the polypeptide.

By "polypeptide" is meant any chain of amino acids, regardless of length or post-translational modification. Typically, a polypeptide may be composed of e.g., six amino acids or more. According to a first embodiment, the polypeptide exhibits immune response-enhancing property and is used as a carrier polypeptide. Examples includes bacterial outer-membrane such as OMP1 or OMP2/3 of *N. meningitidis* or bacterial toxoids such as diphtheria or tetanus toxoid. According to another embodiment, the polypeptide is a biological response modulator and/or a growth factor.

The amino compound can also be a chemical molecule useful as a linker or spacer so that reductive amination produces an activated polysaccharide for further conjugation to a polypeptide which may be chosen as described above. Hereinafter, the terms "aminated polysaccharides" and "activated polysaccharides" are used interchangeably. A chemical molecule useful as a linker or spacer is a bifunctional molecule of formula I: R1-A-R2, wherein R1 is an amino group or a chemical moiety carrying an amino group for example an hydrazide group ie., $NH_2$—NH—CO—; A is an aromatic or preferably, aliphatic chain, substituted or not, e.g., (i) a carbon chain, advantageously a $C_{1-12}$, preferably $C_{2-8}$, more preferably $C_{2-6}$ alkyl or alkylene, or (ii) a dithioalkyl ; and R2 is a functional group able to react with a functional group of a polypeptide, such as an amino, thiol or carboxyl group or any other reactive group such as a succinimidyl or maleimido group. Accordingly, R2 may be independently from R1, an amino group or a chemical moiety carrying an amino group for example an hydrazide group i.e., $NH_2$—NH—CO—. It may also be a thiol, succinimidyl or carboxyl group, or any other group that may react with a linker.

Once a linker is grafted on a polysaccharide by reductive amination, the activated polysaccharide can then be conjugated to a polypeptide per se (chosen as described above), using thiol, amino or carboxyls of the polypeptide. In one embodiment, the linker is a hydrazide, such as adipic dihydrazide (ADH), 4-(N-maleimidomethyl)cyclohexane-1-carboxyhydrazide.HCl.1/2dioxane ($M_2C_2H$), 4(4-N-maleimidophenyl)butyric acid hydrazide.HCl (MPBH) and 3-(2-pyridyldithio)propionyl hydrazide (PDPH). For example, when ADH is used, the activated polysaccharide may conventionally be coupled to carboxyl groups of the polypeptide, in the presence of a carbodiimide such as 1-ethyl 1-3-(3-dimethylaminopropylcarbodiimide) (EDAC).

Chemical molecules useful either as a linker or spacer include for example (i) a dihydrazide alkyl; (ii) an amine for example an amino-thiol alkyl such as cysteine or cysteamine; or (iii) a diamine for example a diamino-thiol alkyl such as cystamine, or a diamino alkyl or alkylene, substituted or not, wherein the alkyl or alkylene is a $C_{1-12}$, preferably $C_{1-8}$, more preferably $C_{1-6}$ alkyl or alkylene. (ADH can also be used as a spacer, but this is not preferred). When such molecules are intended for use as a linker, the activated polysaccharide is accordingly conjugated to an appropriate functional group of a polysaccharide per se. For example, if cystamine is used as a linker, the internal disulfure bound is reduced prior to conjugation and then the activated polysaccharide is coupled to the thiol function of cysteine residues of a polypeptide. In another embodiment, a conventionally be coupled to carboxyl groups of the polypeptide, in the presence of EDAC.

Alternatively, those molecules may be intended for use as a spacer. Once a spacer is grafted onto the polysaccharide, the activated polysaccharide can either (i) be derivatized with a linker and then the activated/derivatized polysaccharide is conjugated to a polypeptide per se; or (ii) be conjugated to a polypeptide previously derivatized with a linker. In this case, the choice of the linker depends upon the nature of the spacer molecule.

For example, if an aminothiol is used as a spacer (e.g., cysteine, cysteamine or cystamnine), it is then suitable to use a linker of formula II: R3-B-R4 wherein R3 is a functional group able to react with a thiol function; B is an aromatic or preferably aliphatic chain e.g., a carbon chain substituted or not; and R4 is a functional group able to react with a thiol, carboxyl or amino group of the polypeptide.

Accordingly, R3 may be a thiol group; a α,β-unsaturated carbonyl or imidyl group, especially a maleimidyl group; an acylhalogen or alkylhalide wherein the halogen atom is Br, Cl or I. R4 is the functional group of the linker which provided for the link to the polypeptide. If the linker is to be reacted with amino groups, R4 is preferably a carboxyl or a succinimidyl such as a N-hydroxy succinimidyl or sulfosuccinimidyl e.g., N-hydroxy sulfosuccinimidyl. If the cross-linking reagent is to be reacted with a thiol group, R4 may be a maleimide group. Chain B comprises from 1 to 12, preferably from 3 to 8 carbon atoms and is more preferably selected from $C_{28}$ alkylene, phenylene, $C_{7-12}$ aralkylene, $C_{2-8}$ alkyl, phenyl, $C_{7-12}$ aralkyl, $C_{1-6}$ alkanoyloxy and benzylcarbonyloxy, wherein alkyl, phenyl, alkylene and phenylene can be substituted or not.

Advantageously, a compound of formula II is a succinimidyl—maleimido alkyl compound, so that the maleimide moiety be reacted with the thiol function of the spacer and the succinimidyl moiety be reacted with the amino groups present on the polypeptide. Such succinimidyl—maleimido alkyl compounds include e.g., N-γ-maleimidobutyryloxy) succinimide ester or sulfosuccinimide ester (GMBS or sulfo-GMBS), maleimido-caproic-N-hydroxysuccinimide ester (MCS), succinimidyl-4-(p-maleimidophenyl)-butyrate (SMPB), sulfo-SMPB, m-maleimidobenzoyl-N-hydroxysuccinimide ester (MBS), maleimido-benzoyl-N-hydroxysulfosuccinimide ester (sulfo-MBS), succinimidyl4-(N-maleimidomethyl) cyclohexane-1-carboxylate (SMCC), sulfo-SMCC.

If a diaminoalkyl is used as a spacer, the linker suitably is a succinimidyl compound such as disuccinimidyl suberate (DSS), bis (sulfosuccinimidyl) suberate (BS3), disuccinimidyl glutarate (DSG), succinimidyldiester of adipic acid (SIDEA), succinimidyldiester of succinic acid (SIDES). In this case, the linker is reacted with the amino groups of the polypeptide. Succinimidyl—maleimido alkyl compounds as described above, may also be used:in this case the linker is reacted with the thiol groups of the polysaccharide.

Accordingly, the invention also provides a conjugation method which comprises performing the reductive amination method of the invention so that an activated polysaccharide is obtained and then reacting the activated polysaccharide with a polypeptide according to one of the procedures described above, so that a polysaccharide-polypeptide conjugate is obtained.

Additionally, it is well within the understanding of the skilled artisan to choose the appropriate reaction conditions to practice the instant invention, given the general guidelines provided herein, ie., specifically with respect to the choice of polysaccharide and protein of interest, aminating agents, reducing agents, buffer conditions and appropriate reaction times, without departing from the spirit of scope of the invention.

The invention also provides:

(i) A pharmaceutical composition for use in therapy or prophylaxis (e.g. a vaccine composition) comprising a polysaccharide-polypeptide conjugate obtained by a conjugation method of the invention and optionally, a pharmaceutically or veterinarily acceptable carrier or diluent.

(ii) A method for immunizing against a pathogen, which comprises administering a polysaccharide-polypeptide conjugate prepared by the conjugation process of the invention, to a mammal in need of such treatment, in a sufficient amount for inducing an immune response against the pathogen in such mammal; the polysaccharide being specific for the pathogen.

More generally, the compositions of the invention can be prepared in accordance with standard techniques well known to those skilled in the pharmaceutical or veterinary art. Suitable carriers or diluents can be water or a buffered saline, with or without a preservative. The conjugate may be lyophilized for resuspension at the time of administration or can be in solution. Compositions of the invention can typically contain an adjuvant. In human applications, alum (aluminum phosphate or aluminum hydroxide) is a typical adjuvant. Saponin and its purified component Quil A, Freund's complete adjuvant and other adjuvants used in research and veterinary application.

Such compositions can be administered by conventional routes, in dosages and by techniques well known to those skilled in the medical or veterinary arts taking into consideration such factors as the breed or species, age, sex, weight, genetics and condition of the particular patient, and the route of administration.

A better understanding of the present invention and of its many advantages will be had from the following non-limiting Examples, given by way of illustration.

EXAMPLE 1

Reductive Amination of Acidic (Negatively Charged) Polysaccharides

Vi polysaccharide from *Salmonella typhi* is a polysaccharide with a net negative charge having the following general structure: [βD GalcA pN Ac 3—O—Ac(1→4)—]. This polysaccharide was extracted from *Salmonella typhi* essentially as described by Gotschlich et al, Prog. Immunobiol. Standard (1972) 5:485 and depolymerized according to the method described in WO 9317178 to a mean molecular weight of 70,000. A dry power was diluted to a final concentration of 12 mg/ml in phosphate buffer 0.02 M pH 7.5. Reaction samples were prepared as follows: To 3.2 ml of the polysaccharide solution was added 400 µl of a diaminohexane solution at 100 mg/ml in phosphate buffer 0.02 M pH 7.5 and 400 µl of solution of cyanoborohydride at 10 mg/ml in phosphate buffer 0.02 M pH 7.5.

The samples were incubated for 15, 30 or 60 min or 48 hours, either (i) in a water bath at 50° C. or (ii) in the SYNTHEWAVE™ 402 the microwave apparatus in which the maximal temperature is set at 50° C. with microwave radiation (radiating power: 15 W).

Then the polysaccharide was purified using 80% alcoholic precipitation followed by size exclusion chromatography on Biogel P6: 440 µl of NaCl 5 M and 18 ml of ethanol were added to the reaction medium and the solution was centrifuged; the pellet was recovered and dissolved in 10 ml NaCl 0.05 M; the solution was loaded on a P6 column; sugar containing fractions were collected and pooled.

The purified preparation was analysed as follows: The efficiency of the reductive amination was evaluated while measuring the rate of amino groups attached on the polysaccharide. To this end, the total sugars were measured according to Dubois et al, Anal. Chem. (1956) 3:350 and the amino groups were measured according to Saifer et al, Clin. Chim. Acta (1960) 5:131. Reductive amination is reaction known to generate, apart from the desirable aminated form, others products including the original non-reduced product and importantly, degradation products. In order to evaluate the amount of degradation products, the percentage of residual reducing sugars was measured according to Park & Johnson, J. Biol. Chem. (1949) 181:149. Results are set forth in Table 1.

TABLE 1

|  | µmoles $NH_2$/mg PS (% residual reducing sugars) | |
| --- | --- | --- |
| Reaction Time | Microwave (50° C.) | Waterbath (50° C.) |
| 15 min | 6.3 (74) | |
| 30 min | 6.3 (78) | |
| 60 min | 6.3 (79) | 0.8 |
| 48 hr | | 8.3 (23) |

These data reveal that the reductive amination achieved under microwave radiation, reaches a plateau within 15 minutes, yielding an aminated polysaccharide product comparable to that obtained after 48 hours in the water-bath. Additionally, they reveal that the percentage of residual reducing sugars remain much higher when reductive amination is conducted under microwave radiation, indicating that less secondary pathway compounds are formed in these conditions, compared to what occurs in the conventional water bath.

Another notable difference in the product of the reactions is the extent to which residual reduced sugar residues remain at the end of the reaction. Very little residual reducing sugar remains following incubation for extended time periods in the water bath, presumably because this reaction proceeds, over time, to development of undesirable degradation. In striking contrast to this is the result obtained in the microwave, in which a substantial proportion of residual reduced sugars remain, and are thus available for successive rounds of reductive amination.

It was also checked that no depolymerization occurred and that no additional reducing sugar is formed during the microwave treatment.

EXAMPLE 2

Reductive Amination of Polysaccharides by Sequential or Successive Reaction Procedures Polygalacturonic acid has the following general structure: [βD GalcA p(1→4)-] Polygalacturonic acid (mean molecular weight, 50,000 equivalent dextran) obtained from Sigma, was dissolved in 0.05 M borate buffer, pH 8.5 to a final concentration of 12 mg/ml. Four hundred µl of diaminohexane (100 mg/ml in 0.05 M borate buffer, pH 8.5) and 400 µl of cyanoborohydride (10 mg/ml in 0.05 M borate buffer, pH 8.5) were added and the mixture was incubated either in the microwave apparatus for 15 or 30 min as described in Examples 1 and 2 or in a 50° C. water bath. Then, the polysaccharide submitted to reductive amination under microwave radiation was purified from the reagents as described in Example 1 and the purified polysaccharide was submitted again to reductive amination as described above.

Alternatively, diaminohexane was added to the polysaccharide, the mixture incubated for 30 min in the microwave apparatus and then cyanoborohydride was added and the mixture incubated for an additional 15 minutes.

In each experiment, the polysaccharide was purified as described and analysed as described in Example 1. The results are set forth in Table 2 below.

TABLE 2

|  | µmoles $NH_2$/mg PS (% residual reducing sugars) | |
| --- | --- | --- |
| Reaction Time | Microwave (50° C.) | Waterbath (50° C.) |
| a) 15 min (three component mixture) | 8.5 | |
| b) 30 min (three component mixture) | 9 (72) | |
| c) 2 successive aminations as in b) | 18 (63) | |
| d) 30 min (imine formation) + 15 min (reduction) | 35 (67) | |
| e) 48 hrs | | 42.5 (11) |

These data reveal that it is possible to increase the extent of amination simply by subjecting the polysaccharide to successive rounds of reductive amination or by performing the two reaction steps separately.

EXAMPLE 3

Effect of Microwave Radiation on Reductive Amination of Neutral Polysaccharides

Dextran is a neutral polysaccharide with the following general structure:[-αD Glc p(1→6)-]. Dextran species having a mean molecular weight of 264,000 (Sigma) was dissolved in phosphate buffer (0.02 M pH 7.5) or a borate buffer (0.05 M pH 8.2) to a concentration of 50 mg/ml. Reaction mixtures prepared as follows: To 3.2 ml of this solution, were added 400 µl of diaminohexane (100 mg/ml in phosphate or borate buffer) and 400 µl of sodium cyanoborohydride (10 mg/ml in phosphate or borate buffer). Samples were incubated at 50° C., either in a water bath or in the SYNTHEWAVE™ 402 microwave apparatus, for lengths of time indicated in Table 3 below. In the microwave apparatus, the maximal temperature is set at 50° C. with microwave radiation (radiating power: 15 W).

Then the polysaccharide was purified and analysed as described in Example 1. Results are to be seen in Table 3:

TABLE 3

| Reaction Time | μmoles NH$_2$/mg polysaccharide (% residual reducing sugars) | | | |
|---|---|---|---|---|
| | Microwave (50° C.) | | Waterbath (50° C.) | |
| First set (phosphate buffer) | | | | |
| 1 hr | 1.8 | (85) | 2.0 | |
| 48 hrs | | | 8.9 | (10) |
| Second set (borate buffer) | | | | |
| 1 hr | 6.0 | | 1.5 | |
| 48 hrs | | | 9.0 | (37) |

By 1 hour, the degree of amination (expressed as μmole NH$_2$/mg polysaccharide) achieved under microwave radiation was higher when the borate buffer was used. In contrast, the degree of amination achieved in the water bath is similar when either buffer is used. Importantly, the microwave does accelerate the reductive amination of dextran in borate buffer.

EXAMPLE 4

Non-ionic Polysaccharides Containing N-acetyl Groups but no Net Charge

Pneumococcal polysaccharide type 14 is a neutral polysaccharide with N-acetyl groups. It was prepared from *Streptococcus pneumoniae* type 14 according to the method of Gotschlich et al (supra) and depolymerized according to WO 93/7178 to a mean molecular weight of 60,000 equivalent dextran; A dry power was dissolved in either borate buffer 0.02 M pH 8.5 or phosphate buffer 0.02 M pH 8 to a final concentration of 12 mg/ml. Then it is proceeded as described in Example 1 above. The results are set forth in Table 4 below.

TABLE 4

| Reaction Time | μmoles NH$_2$/mg PS (% residual reducing sugars) | | | |
|---|---|---|---|---|
| | Microwave (50° C.) | | Waterbath (50° C.) | |
| 30 min (phosphate) | 20.5 | (71) | | |
| 60 min (phosphate) | 25 | (78) | | |
| 48 hrs (phosphate) | | | 18 | (51) |
| 30 min (borate) | 7.5 | (72) | | |
| 4 hrs (borate) | 17 | (78) | | |
| 48 hrs (borate) | | | 24 | (48) |

This reveals that the phosphate buffer favours the reductive amination under microwave radiation, while the borate buffer is preferred for performing the reductive amination in a water bath. Accordingly, choice of buffer is critical to optimize the reaction. The highest degree of reductive amination was obtained after 30–60 minutes in the microwave in phosphate buffer.

The fact that a non-ionic polysaccharide is able to react very efficiently under microwave radiation suggests that not only ionic charges but also the conformation of the molecule or the presence of a particular chemical group can confer an overall dipole moment.

What is claimed is:

1. A method of reductive amination of polysaccharides that comprises:
   (i) subjecting a reaction mixture comprising a polysaccharide, an amino compound and a reducing agent, to microwave radiation for a period of time sufficient to aminate the polysaccharide;
   (ii) (a) subjecting a reaction mixture comprising a polysaccharide and an amino compound to microwave radiation for a period of time sufficient to allow the formation of an imine compound, (b) adding a reducing agent to the reaction mixture obtained in (a) so that the polysaccharide is aminated;
   (iii) (a) adding an amino compound to a polysaccharide so that an imine compound is formed, (b) adding a reducing agent to the reaction mixture obtained in (a) and, (c) subjecting the reaction mixture obtained in (b) to microwave radiation for a period of time sufficient to aminate the polysaccharide; or
   (iv) (a) subjecting a reaction mixture comprising a polysaccharide and an amino compound to microwave radiation for a period of time sufficient to allow the formation of an imine compound, (b) adding a reducing agent to the reaction mixture obtained in (a) and, (c) subjecting the reaction mixture obtained in (b) to microwave radiation for a period of time sufficient to aminate the polysaccharide.

2. A method according to claim 1, wherein the microwave radiation is applied to the reaction mixture in a focused or locaiized manner.

3. The method according to claim 1, wherein the period of time is from 10 minutes to 4 hours.

4. The method according to claim 1, wherein the reaction mixture is in a buffer solution.

5. The method according to claim 1, wherein the polysaccharide is partially aminated.

6. The method according to claim 1, wherein the polysaccharide is partially aminated, and the method further comprises purifying the partially aminated polysaccharide and subjecting the purified partially aminated polysaccharide according to the method of claim 1 to further aminate the partially aminated polysaccharide.

7. The method according to claim 1, wherein the polysaccharide is a bacterial or fungal polysaccharide.

8. The method according to claim 7, wherein the polysaccharide is a bacterial polysaccharide that is a capsular polysaccharide or the O-antigen moiety of a lipopolysaccharide.

9. The method according to claim 8, wherein the polysaccharide is prepared from the group consisting of *S. pneumoniae, H influenzae, N meningitidis, E. coil, S. typhi, S. mutans, C. typhimurium, C. neoformans, K. pneunoniae, S. aureus*, and *P. aeruginosa*.

10. The method according to claim 1, wherein the reducing agent is cyanoborohydride or pyridine borane.

11. The method according to claim 1, wherein the amino compound is a polypeptide and the reductive amination reaction results in the formation of a polysaccharide-polypeptide conjugate.

12. The method according to claim 1, wherein the amino compound is a linker and the reductive amination reaction results in the formation of an activated polysaccharide.

13. The method according to claim 12, which further comprises reacting the activated polysaccharide with a polypeptide such that a polysaccharide-polypeptide conjugate is obtained.

14. The method according to claim 1, wherein the amino compound is a spacer, such that the reductive amination reaction results in the formation of an activated polysaccharide.

15. The method according to claim 14, which further comprises reacting the activated polysaccharide with a derivatized polypeptide, such that a polysaccharide-polypeptide conjugate is obtained.

16. A pharmaceutical composition comprising a polysaccharide-polypeptide conjugate produced according to claim 11, 13 or 15.

17. The method according to claim 12, wherein the linker is a hydrazide.

18. The method according to claim 14, wherein the spacer is an amino-thiol alkyl or a diamine.

* * * * *